United States Patent [19]

Dolbeare et al.

[11] Patent Number: 4,780,406

[45] Date of Patent: * Oct. 25, 1988

[54] FLOW CYTOMETRIC MEASUREMENT OF TOTAL DNA AND INCORPORATED HALODEOXYURIDINE

[75] Inventors: Frank A. Dolbeare; Joe W. Gray, both of Livermore, Calif.

[73] Assignee: The Regents of the University of California, Berkeley, Calif.

[*] Notice: The portion of the term of this patent subsequent to Apr. 29, 2003 has been disclaimed.

[21] Appl. No.: 617,655

[22] Filed: Jun. 5, 1984

Related U.S. Application Data

[63] Continuation-in-part of Ser. No. 542,955, Oct. 18, 1983.

[51] Int. Cl.[4] .............................................. C12Q 1/68
[52] U.S. Cl. ............................................. 435/6; 435/7; 435/29; 435/91; 436/56; 436/63; 436/94; 436/800; 935/76; 935/77
[58] Field of Search .......................... 435/6, 7, 29, 91; 436/63, 94, 56, 800; 935/76, 77

[56] References Cited

PUBLICATIONS

Schwartz, Biochemistry, vol. 15, no. 14, (1976) pp. 3097–3105.
Dolbeare, et al., Clin. Chem., vol. 23, No. 8, (1977), pp. 1485–1491.
Gratzner, Science, vol. 218, (1982), pp. 474–475.
Gratzner, et al., Cytometry, vol. 1, No. 6, (1981), pp. 385–389.
Noguchi, et al., Cytometry, vol. 1, No. 6, (1981), pp. 390–393.
Gordon, et al., J. Immunol., vol. 127, No. 4 (1981), pp. 1634–1639.

*Primary Examiner*—Christine M. Nucker
*Assistant Examiner*—Stephen C. Wieder
*Attorney, Agent, or Firm*—Stephen C. Macevicz; Shyamala T. Rajender; Berthold J. Weis

[57] ABSTRACT

A method for the simultaneous flow cytometric measurement of the total DNA content and the level of DNA synthesis in normal and malignant cells is disclosed. The sensitivity of the method allows a study of cell cycle traverse rates for large scale cell populations as well as single cell measurements. A DNA stain such as propidium iodide or Hoechst 33258 is used as the probe for the measurement of total DNA content and a monoclonal antibody reactive with a DNA precursor such as halodeoxy-uridine (HdU), more specifically bromodeoxyuridine (BrdU) is used as a probe for the measurement of HdU or BrdU uptake by the cells as a measure of DNA synthesis.

23 Claims, 9 Drawing Sheets

FLOW CYTOMETRIC MEASUREMENT OF TOTAL DNA AND INCORPORATED HALODEOXYURIDINE

The United States Government has rights in this invention pursuant to Contract No. W-7405-ENG-48 between the United States Department of Energy and the University of California, for the operation of the Lawrence Livermore National Laboratory.

This is a continuation in part of copending application Ser. No. 542,955 filed Oct. 18, 1983.

BACKGROUND OF THE INVENTION

The present invention relates generally to flow cytometry. More specifically, it relates to the simultaneous measurement of incorporated BrdU and the total cellular DNA content by flow cytometric techniques.

The growth of any tissue at the cellular level is governed by variations in (1) the length of the cell cycle in the fraction of cells that continuously divide, (2) the growth fraction or the fraction of cells in the cell cycle at a given time and (3) the rate of cell loss. All these three mechanisms are important and operative in the growth of normal and malignant cells. A study of the cytokinetic properties of normal and tumor tissues, therefore, aid in the development of effective anticancer strategies for cell-cycle-phase-specific agents.

Cells in the body of an adult animal may be divided into three major categories: (1) differentiated cells i.e., cells which do not divide and proliferate and which eventually die; (2) cells that do not normally divide and therefore do not synthesize DNA but ca be induced to do so by an appropriate stimulus; and (3) continuously dividing cells which actively synthesize DNA and which move around the cell cycle from one mitosis to the next. The life cycle of a continuously dividing cell exhibits three distinct and consecutive phases. There is a period, the $G_1$ phase, during which the cell is preparing for DNA synthesis but no actual, appreciable synthesis occurs. This phase is followed by the S phase, during which DNA is actively synthesized. During this phase, the cells take up nucleic acids present in the surrounding medium or environment, incorporating them into the DNA that is synthesized. The DNA content of the cell is doubled during the S phase. Following the S phase is the $G_2M$ phase during which period the cell prepares for mitosis. No DNA synthesis occurs in the $G_2M$ phase either.

The ability to measure, distinguish and differentiate between cell populations in the above three phases is, therefore, essential for many biological ad biomedical investigations. The cell cycle traverse characteristics of normal and malignant cells, measured as a function of the frequency of DNA synthesizing cells, yield valuable information concerning the treatment prognosis and therapy for various types of cancer. Studies of the cell cycle traverse of drug treated populations also yield valuable information about the mechanism of action of the drug.

S. C. Barranco et al., Cancer Res., 42, 2894 (1982), studied the cell kinetics properties of CHO cells to direct the timing of two-drug combination treatment of normal and tumor cells.

M. G. Pallavicini et al., Cancer Res., 42, 3125 (1982), measured the DNA distribution sequences, tritiated thymidine uptake by tumor cells and the radioactivity of cells labeled with tritiated thymidine prior to and after treatment with 1-beta-D-arabinofuranosylcytosine, a cytotoxic agent.

J. S. Hart et al, Cancer, 39, 1603 (1977), studied the prognostic significance of individual patient characteristics using eight pretreatment variables and reported that cytokinetic factors were important factors in the administration of chemotherapy and were of clinical importance in selecting approaches to therapy.

Coffino et al., Proc. Natl. Acad. Sci., 72, 878–882, (1975), studied the effect of dibutyryl cyclic AMP (dbc-AMP) on the cell cycle traverse of S-49 mouse myeloma cells by measuring DNA distributions and found that the induced cytokinetic changes yielded valuable information about the mechanism of action of the dbc-AMP.

The cell fraction in the S phase may be determined by measuring the uptake of radioactively labeled nucleic acids present in the environment. One of the most commonly used methods is the measurement of the uptake of labeled nucleic acids, such as thymidine, uridine or bromodeoxyuridine which are chemical analogs of thymidine and which are readily incorporated by the cell into its DNA. The presence of the label may be detected by autoradiography or liquid scintillation counting.

H. Quastler and F. G. Sherman, Exp. Cell Res., 17, 420 (1959) reported an analysis of the kinetics of a particular cell population, the different compartments existing in the system, transitions between the compartments which occur regularly, and estimates of the system parameters and individual variations. Their studies indicated that differentiation of the cells in their system occurred only during certain critical phases of the generative cycle.

Flow cytometry has been applied for the measurement of DNA in cultured cells to monitor ploidy of cells and changes in cell growth pattern (M. A. Van Dilla et al, Science, 163, 1213 (1968)).

J. W. Gray et al., in Cell Tissue Kinet., 10, 97 (1977) described a rapid method for the analysis of cell cycle traverse. According to this method, cells in S phase were pulse labeled with a radioactive DNA precursor and the progress of the labeled cells through the cell cycle was monitored by means of the label using flow cytometry and scintillation counting.

Recently, a method for the detection of BrdU incorporation using polyclonal antibodies has been reported by H. G. Gratzner et al., Exp. Cell Res., 95, 88 (1975); H. G. Gratzner et al., J. Histochem. Cytochem., 24, 34 (1976); H. G. Gratzner et al., Res. Comm. Chem. Pathol. Pharmacol., 20, 34 (1978).

Several measurement techniques, such a autoradiography, liquid scintillation counting, cytometric imaging, flow cytometry and the like, which have been developed over the years, suffer from serious limitations. Autoradiography is time consuming and involves laborious measurements. Furthermore, the method is also limited by the difficulty in distinguishing between unlabeled and weakly labeled cells and with background noise.

Scintillation counting which is based on the radiation emissions from the radioactive label, such as tritium, $^{14}C$, $^{32}P$ and the like, requires measurements involving a small fraction of labeled cells in large cell populations and does not lend itself to single cell analysis or measurements. The use of antibodies offers an attractive alternative, but the polyclonal antibodies used exhibit variable specificity depending on the animal used for the immunization and also lack sufficient specificity.

Furthermore, they cross-react with thymidine and are difficult to separate from the other immunoglobulins present in the system.

For the measurement of cell growth patterns, it is necessary to resolve the DNA distribution into its component parts. This analysis is not simple since the population distribution curves for the various phases of the cell cycle are, most often, quite complex due to considerable overlap in the measured DNA distribution between phases and due to inherent shortcomings in the mathematicals models, methods and techniques used.

It would, therefore, be desirable to have a relatively simple technique for completely resolving the DNA distributions in the three major phases of the cell cycle, $G_1$, S and $G_2M$.

SUMMARY OF THE INVENTION

Accordingly, it is an object of the subject invention to provide a simple method for resolving cellular DNA distribution in the three major phases of the cell cycle.

It is another object of the present invention to measure the level of incorporation of DNA precursors as a measure of DNA synthesis during the various phases of the cell cycle.

It is a further object of the instant invention to provide a flow cytometric technique for the simultaneous measurement of the total DNA content of a cell and the level of DNA synthesis during the various phases of the cell cycle.

It is an additional object of the present invention to provide a novel use for monoclonal antibodies reactive with DNA precursors in the measurement of DNA synthesis during various phases of the cell cycle with a simultaneous measurement of the total DNA content of the cell.

Yet another object of the present invention is to provide a method for the measurement of DNA synthesis following drug treatment in cancer therapy.

Still another object is to provide a method for the measurement of the rate of cell cycle traverse.

Additional objects, advantages and novel features of the invention will be set forth in part in the description which follows, and in part will become apparent to those skilled in the artupon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the present invention is directed to a method for the simultaneous flow cytometric measurement of the cellular DNA content and the amount of the uptake of DNA precursors as a measure of DNA synthesis during various phases of the cell cycle. A suitable DNA stain or a fluorescent dye which binds to cellular DNA, such as propidium iodide (PI), serves as a probe for the measurement of the total cellular DNA content while a monoclonal antibodies (mabs) reactive with the DNA precursor of choice serves as a probe for the newly synthesized DNA. The DNA precursor normally utilized in these measurements is a halogenated uridine, preferably bromo-, chloro-, or iododeoxyuridine, which is a chemical analog of thymidine and which is readily taken up by the cells and incorporated into their DNA.

Basically, the method for the simultaneous measurement of total cellular DNA content and of incorporated HdU comprises reacting cells with radioactive labeled HdU; partially denaturing cellular DNA with a denaturing agent; adding to the reaction medium mabs reactive with HdU; reacting the bound mabs with a labeled second antibody; incubating the mixture with a DNA stain; measuring simultaneously the intensity of the DNA stain as a measure of the total cellular DNA and the HdU incorporated as a measure of DNA synthesis. Alternatively, the antibodies against HdU themselves may be labeled with any convenient label, including but not limited to fluorescent labels, radioactive labels, enzyme labels and the like. Although measurements may be conveniently made by flow cytometry, other analytical techniques may also be utilized. The data obtained from the flow cytometric measurements are plotted to form bivariate distributions of DNA content vs. BrdU content. These distributions readily yield the relative amounts of the halodeoxyuridine incorporated into cellular DNA during various phases of the cell cycle, $G_1$, S and $G_2M$ phases. The method also allows for the quantification of low levels of incorporation of HdU and is applicable for both in vivo and in vitro studies. Due to the sensitivity of the measurements, an analysis of both the DNA content and the level of incorporation of HdU in large cell populations as well as in single cells becomes possible.

The subject method is useful in many biological and biomedical investigations such as the detection of the fraction of cells which have synthesized new DNA as part of their proliferation cycles; improved and accurate measurements of proliferation of cells in tumor and normal tissues, particularly monitoring the effects of drugs on proliferation in the course of cancer therapy; the identification of cells that have repaired injury; the detection of unscheduled DNA synthesis; and improved detection of chemicals which are potentially damaging to DNA. The method also provides a more sensitive tool for the detection of chromosome injury thus facilitating monitoring human cells for evidence of genetic injury. The subject invention also provides an assay for incorporated BrdU as compared to the total cellular DNA content and BrdU in solution, particularly in competition ELISA procedures to determine the level of BrdU in serum or in other BrdU containing aqueous solutions.

DESCRIPTION OF THE INVENTION

Figure 1A:
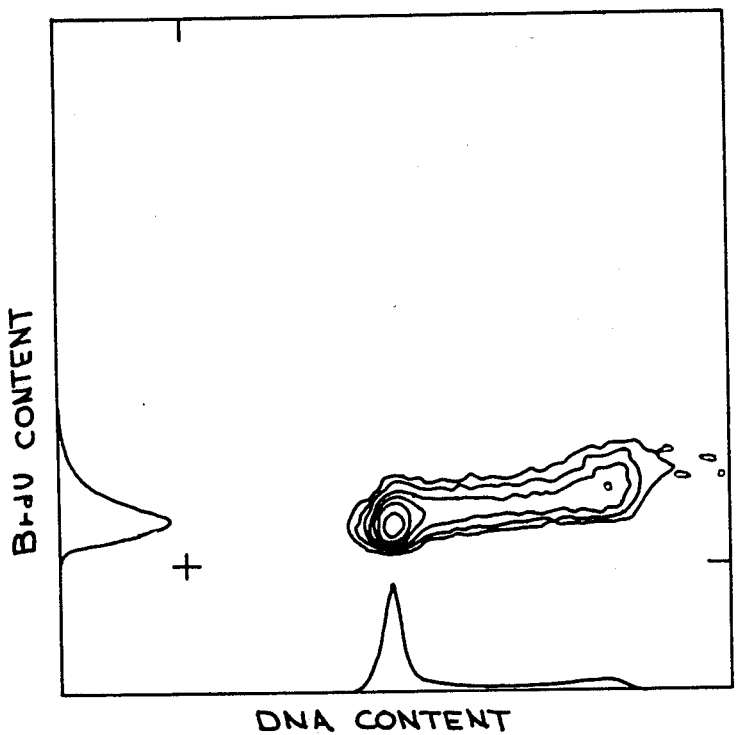
FIGS. 1a and 1b show bivariate DNA/BrdU distributions measured for CHO cells, before and after BrdU pulse.

The present invention is directed to a method for the simultaneous flow cytometric measurement of the cellular DNA content and the amount of the uptake of DNA precursors as a measure of DNA synthesis during various phases of the cell cycle and cell cycle traverse in normal and in malignant cells in vitro and in vivo. A monoclonal antibody reactive with a DNA precursor, such as thymidine or an analog thereof, serves as a probe for newly synthesized DNA during various phases of the cell cycle such as the $G_1$, S and $G_2M$ phases. The DNA precursor normally utilized in these measurements is a halogenated uridine, preferably, bromo-, chloro-, or iododeoxyuridine, which is a chemical analog of thymidine, a natural DNA nucleic acid. Halodeoxyuridine (HdU) is readily taken up by the cells and incorporated into their DNA in the place of thymidine.

The method for the simultaneous measurement of the total cellular DNA content and of incorporated HdU essentially comprises reacting cells with HdU; partially denaturing cellular DNA with a suitable denaturing agent; adding to the reaction medium monoclonal antibodies (mabs) reactive with HdU; reacting the bound mabs with a labeled second antibody; incubating the mixture with a DNA stain; measuring simultaneously the intensity of the DNA stain as a measure of the total cellular DNA and the HdU incorporated as a measure of DNA synthesis.

Although measurements ma be conveniently made by flow cytometry, other analytical techniques may also be utilized. The data obtained from the flow cytometric measurements are plotted to form bivariate distributions of DNA content vs. BrdU content. These distributions readily yield the relative amounts of the halodeoxyuridine (HdU) incorporated into cellular DNA during various phases of the cell cycle, namely, $G_1$, S and $G_2M$ phases. The method also allows for the quantification of low levels of incorporated HdU and is applicable for both in vivo and in vitro studies. The sensitivity of the measurements enables an analysis of both the DNA content and the level of incorporation of HdU in large cell populations as well as in single cells becomes possible.

A critical aspect of the invention is the partial denaturation of the cellular DNA to facilitate the accessibility of monoclonal antibodies to the incorporated HdU since the antibodies do not bind to HdU in double stranded DNA. While any suitable denaturants may be utilized, formamide in combination with heat (about 80° C.) and HCl, preferably, about 1.5M HCl are the denaturants of choice. Formamide at a temperature of about 80° C. is the preferred denaturant because it exposes more of the incorporated HdU to the mabs thereby increasing the sensitivity of the measuring technique. Formamide in combination with an elevated temperature also serves as a better denaturant for solid tumor tissue. Bone marrow cells, however, appear to be more prone to destruction by formamide at elevated temperatures and, therefore, for bone marrow cells, HCl is the recommended denaturant.

For the measurement of the total cellular DNA content, propidium iodide (PI) or the dye identified as Hoechst 33258 (blue fluorescence) is used as the probe. Since PI also stains the RNA in the cell, it is necessary to remove the RNA content of the cell by acid or enzymatic hydrolysis when PI is used as the DNA stain. The HCl treatment not only partially denatures the DNA to facilitate antibody binding but also hydrolyzes RNA thereby eliminating separate RNAse or similar enzyme treatment. However, enzymatic hydrolysis of DNA is required when formamide in combination with heat is used for the denaturing process.

A monoclonal antibody reactive with a DNA precursor, such as thymidine or an analog thereof, serves as a probe for newly synthesized DNA during various phases of the cell cycle such as $G_1$, S and $G_2M$. The DNA precursor normally utilized in these measurements is a halogenated uridine, preferably bromo-, chloro-, or iododeoxyuridine, which is a chemical analog of thymidine. Halodeoxyuridine (HdU) is readily taken up by the cells and incorporated into their DNA in the place of thymidine.

The data obtained from the flow cytometric measurements are plotted to form bivariate distributions of DNA content vs. BrdU content. These distributions readily yield the relative amounts of the halodeoxyuridine incorporated into cellular DNA during various phases of the cell cycle, $G_1$, S and $G_2M$ phases. The method also allows for the quantification of low levels of incorporation of HdU and is applicable for both in vivo and in vitro studies. The sensitivity of the measurements, makes possible an analysis of both the DNA content and the level of incorporation of HdU in large cell populations as well as in single cells.

A preferred embodiment of the method of the subject invention for the simultaneous measurement broadly involves labeling cells with HdU, preferably with BrdU, CldU or IdU, still more preferably with BrdU, denaturing the DNA with formamide and elevated temperatures (about 80° C.) or with HCl, preferably about 1.5M HCl, reacting the HdU-labeled cells, preferably BrdU-or IdU-labeled cells with monoclonal antibodies reactive with HdU or more specifically, with BrdU or IdU, incubating the cells with a second antibody conjugated to a second label such as an enzyme, preferably horse radish peroxidase or beta-galactosidase, or a fluorescent dye, such as fluorescein or rhodamine, removing the excess of unbound, labeled second antibody, staining the cells with an appropriate DNA stain such as propidium iodide or Hoechst 33258 dye which binds to the total DNA of the cell, measuring the level of the bound, labeled second antibody as a measure of the HdU or more specifically BrdU or IdU incorporated, and measuring the intensity of the bound propidium iodide or Hoechst 33258, as a measure of the total DNA content of the cell. The HdU, more specifically the BrdU or IdU may also be independently labeled for convenience. Any suitable label may be employed. These labels include but are not limited to fluorescent labels, chromophores, radioactive labels, enzyme labels and the like. Any labeling technique may be used. Pulse labeling is a method of choice for convenience.

The radioactivity of the bound, radioactive HdU is measured by liquid scintillation counting and compared and correlated with the level of HdU incorporation as measured by antibody binding.

The bivariate distribution of the total DNA and newly synthesized DNA, as measured by the incorporation of HdU, through the various phases of the cell cycle before and after drug treatment of an animal, may be used to monitor the effects of the drug in cancer or other types of therapy. The method for the measurement of HdU incorporation following drug treatment of an animal typically comprises treating the animal with the drug; administering HdU, optionally labeled with labels such as radionuclides, to the drug-treated animal; selectively removing cells from various organs of the body of the animal; reacting the cells with mabs reactive with HdU; incubating the cells with a second antibody conjugated to a label; incubating the cells with a suitable DNA stain; measuring simultaneously at specified time intervals the bound HdU and the bound DNA stain cytometrically or spectrophotometrically as a measure of the incorporated HdU and of the total DNA in the cells; and analyzing the bivariate distribution of total DNA and bound BrdU through the various phases of the cell cycle to determine the level of HdU incorporation as measure of new DNA synthesis. The HdU may be BrdU, CldU, or IdU, preferably BrdU or IdU. The HdU may also be optionally labeled with any suitable label. Exemplary labels are enzymes, fluorescent dyes, radionuclides and the like. Enzymes and fluorescent dyes are most conveniently employed. Fluorescein and rhodamine are the dyes of choice; and horse radish peroxidase and beta-galactosidase are the enzymes of choice. The same list of labels may also be used on the second antibody. The HdU, the total DNA and the second antibody, all three of them may be labeled in the same experiment and monitored independently or in combination through the cell cycle traverse.

Monoclonal antibodies reactive with HdU are prepared according to the method described by M. Vanderlaan et al., in copending DOE Case No. S-60,122 (RL-9069), Provisional Ser. No. 542,967, deposit date Oct. 18, 1983, which is incorporated herein by reference. The second antibody is usually goat antimouse antibody. The label on the second antibody may be a fluorescent dye, a chromophore, a radionuclide or an enzyme. Exemplary fluorescent molecules are fluorescein and rhodamine and exemplary enzymes are alkaline phosphatase, peroxidase, preferably horse radish peroxidase and beta-galactosidase. When fluorescent molecules are used as the tags, the fluorescence intensities are measured by a flowcytometer, fluorometer or a spectrophotometer. When enzymes are used as the labels, measurements are made by standard ELISA techniques as described by M. Vanderlaan et al., supra. When peroxidase is the enzyme of choice, $H_2O_2$ is the substrate; when alkaline phosphatase is the enzyme used, the substrate is p-nitrophenyl phosphate; and when beta-galactosidase is the enzyme, p-nitrophenyl-beta-D-galactopyranoside is the preferred substrate. Fluorescein is the preferred label on the second antibody When fluorescein is used as the label on the second antibody and PI is used as the DNA stain, the bound HdU, typically BrdU, is measured by measuring the fluorescence intensity of the fluorescein label at about 520 nm (low green) and the propidium iodide as a measure of the total DNA is measured in terms of its fluorescence intensity at about 600 nm (red). A combination of stains on the various experimental components may also be employed for ease of measurement. Typically, Hoechst 3258 may be used as the DNA stain, in combination with fluorescein as the marker for BrdU and rhodamine as the label for the second antibody. The fluorescence intensities of all three labels may be measured and the amount of total DNA and incorporated BrdU determined by a combination of these measurements for greater accuracy.

The measurements are conveniently made using a flow cytometer and the data obtained are arranged to form bivariate distributions of DNA content vs. HdU content. These distributions readily yield the relative amounts of HdU incorporated during various phases of the cell cycle and the total DNA content of the cell. Analysis of the data yield information about cell cycle traverse and of the kinetics of DNA synthesis. The method of the subject invention is so sensitive that extremely low levels of BrdU may be readily quantified. Flow cytometry allows large populations of cells to be processed in a short period of time such that reliable studies of small subpopulations are made possible.

The following examples are presented by way of example only and are not to be construed as limiting the scope of the invention in any manner. Although Chinese Hamster Ovary (CHO) cells and mice hematopoietic cells were used in the experiments which are described hereinbelow, other types of cells, including cells from human sources and human tumor cells, may be conveniently used in the subject method.

EXAMPLE 1

CHO Cell Culture

Chinese hamster ovary (CHO) cells were grown in suspension culture in a one liter spinner flask in minimum essential alpha medium (alpha-MEM) with 10% fetal calf serun (FCS), to a density of $2 \times 10^5$/ml. Bromodeoxyuridine (BrdU) was then added to the cell suspension to a final concentration of 10 uM. After 10 min the cells were spun down, washed once in phosphate buffered saline (PBS, pH 7.2) and resuspended in 100 ml PBS. The cells were then fractionated on the basis of size using a JE-6B elutriator rotor driven by a Beckman J2-21 centrifuge. Elutriation was carried out at room temperature with fractions collected on ice. Approximately $2 \times 10^8$ cells were loaded at a sedimentation velocity of 5.0 mm/hr$\times$g, with a constant flow rate of 20 ml/min. Thereafter, the sedimentation velocity was increased in increments of 0.5 mm/hr$\times$g with each collected fraction volume of 250 ml. Cells were then pelleted and resuspended in 70% EtOH. Elutriated fractions were stained for DNA and incorporated BrdU, using propidium iodide and mouse monoclonal anti-BrdU-antibodies; the mouse antibodies were reacted with conjugated with fluoresceinated goat anti-mouse IgG as described in Examples 2 and 3 infra.

EXAMPLE 2

In Vitro Experiments with CHO Cells

In one set of experiments, CHO cells growing exponentially in alpha-MEM with 10% FCS at $3 \times 10^5$ cells/ml were treated for 30 min with 10 uM BrdU. The cells were then refed with conditioned medium from a second untreated spinner flask. Twenty milliliter aliquots were removed at 2-hr intervals, counted, washed with PBS ($P_i$/NaCl, pH 7.2), and fixed for at least 30 min in cold 70% ethanol (EtOH); and analyzed flow cytometrically.

In a second series of experiments, exponentially growing CHO cells were treated with [$^3$H]BrdU for 30 min (specific activity, 35 Ci/mmol; 1 Ci$=3.7 \times 10^{10}$Bq; final concentration, 1 uCi/ml). The cells were then harvested, washed in $P_i$/NaCl, and fixed for at least 30 min in cooled 70% EtOH and analyzed as in Experiment 1.

In another series of experiments, the same procedure as in Examples 1 and 2 was repeated with mouse KHT tumor cells.

EXAMPLE 3

In Vivo Mice Experiments

Control and 1-beta-D-arabinofuranosylcytosine (araC) treated female C3H mice were injected intraperitoneally with 50 mg of BrdU per kg one hour prior to sacrifice. araC-treated mice received BrdU 3, 6 and 9 hrs after a single intraperitoneal injection of 500 mg of araC per kg. The femurs of each mouse were removed and the hematopoietic cells were harvested by flushing with 1 ml of alpha-MEM. The recovered cells were then resuspended by pipeting, filtered through 37 um mesh, and fixed with 70% EtOH, reacted with mabs, stained with PI, and analyzed.

EXAMPLE 4

Monoclonal antibodies (mabs) to HdU, more specifically to BrdU, CldU or IdU were prepared according to the method of M. Vanderlaan et al., described in co-pending DOE Case No. S-60,122 (RL-9069), Provisional Ser. No. 542,967, deposit date Oct. 18, 1983, which description is incorporated herein by reference and made a part hereof. The two hybridomas which continuously secrete the mabs reactive with HdU are designated IU-1 and IU-2 and are on deposit with the American Type Culture Collection, 1230 Rocklawn Drive, Rockville, Md. and are accorded ATCC Accession Nos. HB-21 and HB-20 respectively. As used herein, however, the terms IU-1 and IU-2 refer not only to the hybridomas producing the mabs but also interchangeably to the mabs reactive with HdU. While IU-1 and IU-2 were used in these experiments, any other suitable antibody reactive with HdU, more specifically with BrdU or IdU or CldU, may be prepared and used.

EXAMPLE 5

Cytochemistry

The cells were removed from ethanol, resuspended in 2 ml of 1.5M HCl at 20° C. for 20 min, washed twice with 5 ml of $P_i$/NaCl, and resuspended for 1 hr in $P_i$/NaCl solution containing 0.5% Tween 20, 0.5% bovine serum albumin (BSA) and a 1:200 dilution of monoclonal anti-BrdU. The cells were then washed twice with $P_i$/NaCl and resuspended for 30 min in a solution containing $P_i$/NaCl, 0.5% Tween 20, a 1:100 dilution of a stock solution of fluorescein-labeled goat anti-mouse gamma globulin and 1% neutral goat serum (to prevent nonspecific adsorption of the fluorescein-labeled anti-mouse gamma globulin). The cells were then washed twice with 5 ml of $P_i$/NaCl and resuspended in 1 ml of $P_i$/NaCl containing 5 ug of PrdI per ml. After 1 hr, the cells were ready for flow cytometric analysis.

EXAMPLE 5

Flow Cytometry and Cell Sorting

Cell analysis was performed with a flow cytometer, designed and built at the Lawrence Livermore National Laboratory. Cell sorting was accomplished by using a fluorescence-activated cell sorter. During flow cytometry, cells were excited at 488 nm. Red fluores cence from PI was collected through a 600 nm long wavelength pass filter and recorded as a measure of total DNA content and green fluorescence from fluorescein was collected through a 514 nm bandpass filter and recorded as a measure of the amount of incorporated BrdU. The resulting data were accumulated to from a bivariate $64 \times 64$ channel distribution showing the distribution of DNA (red fluorescence) and BrdU (green fluorescence) among the cells of the population.

Cells were sorted from several regions of the bivariate DNA/BrdU distribution measured for CHO cells treated for 30 min with [$^3$H]BrdU. Sorting regions are indicated in FIG. 2a. Ten thousand cells were sorted from each region directly into liquid scintillation vials. The radioactivity per cell was determined in the manner described by J. W. Gray et al., J. Cell Physiol., 108, 135 (1981).

Figure 1B:
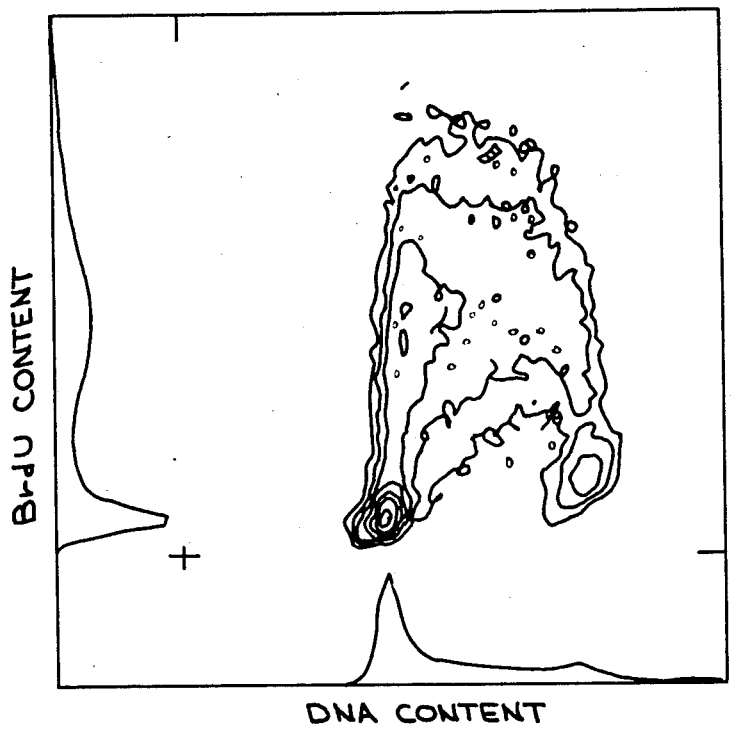

FIG. 1 shows the bivariate DNA/BrdU distributions measured for exponentially growing CHO cells before and after BrdU treatment. FIG. 1A is a diagram of the DNA/BrdU distribution prior to BrdU treatment and FIG. 1B shows the same DNA/BrdU distribution after a 30 min BrdU pulse. The abscissae and the ordinates show univariate frequency distributions for the total DNA (red fluorescence) and the amount of incorporated BrdU (green fluorescence) respectively. The point of origin of each contour plot is indicated with a cross. It can be seen that although all three phases of the cell cycle, the $G_1$, S and $G_2$ phases show some BrdU incorporation (green fluorescence), there is a wide variation in BrdU incorporation, the S-phase cells in the labeled population showing a substantially larger level of BrdU incorporation (green fluorescence. The red fluorescence, indicatig the total DNA content is about the same in all three phases. The bivariate distribution also indicates a variation in the rate of BrdU incorporation across S phase, the mid-S phase showing the highest level and the early and late S phase showing the lower levels.

Figure 2:
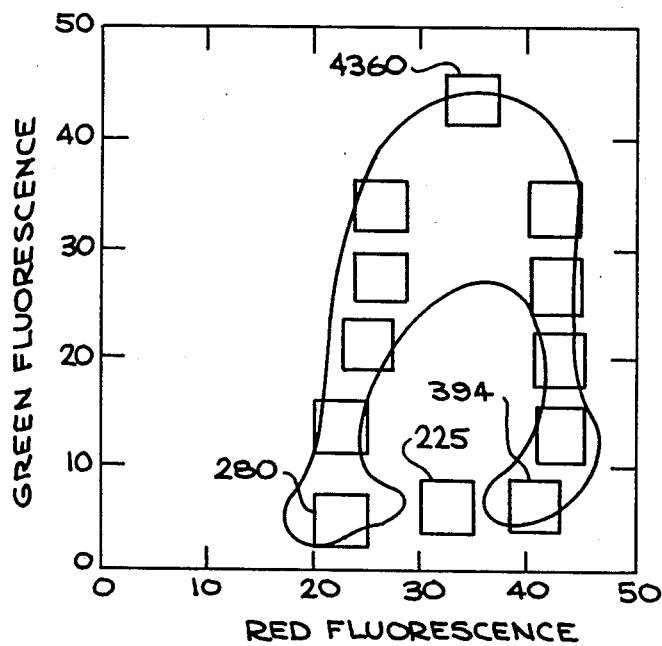
FIG. 2 is a bivariate DNA/BrdU distribution diagram for CHO cells after a [$^3$H]BrdU treatment.

FIG. 2 shows a plot of the green fluorescenc intensity as a measure of BrdU incorporation vs. red fluorescence intensity as a measure of the total DNA content and the regions from which cells were sorted for liquid scintillation counting to measure the radio-activity per cell. The level of BrdU incorporated was measured by both mab binding and radioactivity of the bound [$^3$H]BrdU.

Figure 3:
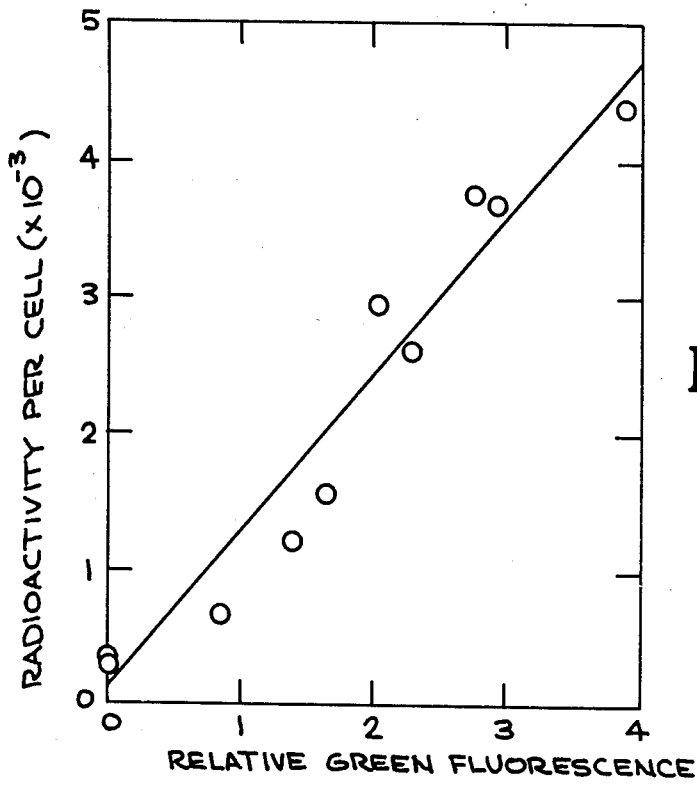
FIG. 3 illustrate bivariate DNA/BrdU distributions measured for CHO cells at intervals of two hours.
Figures 4A, 4B, 4C:
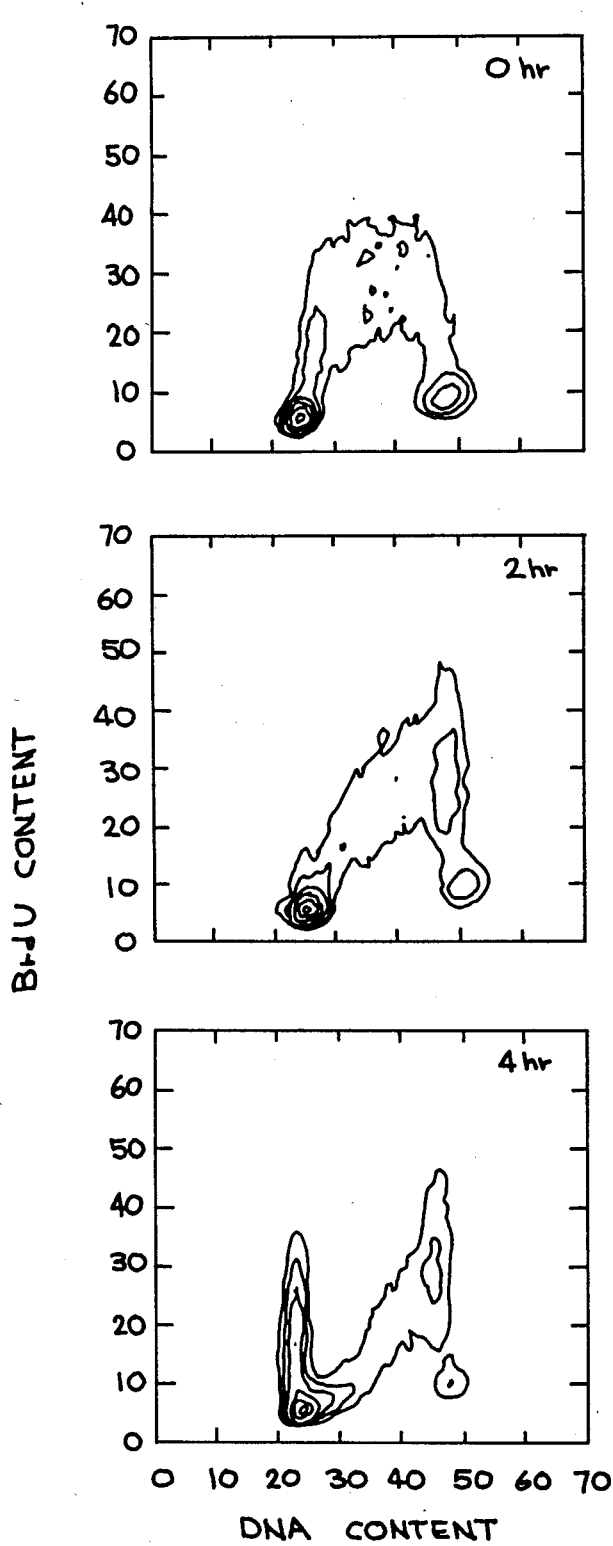
FIG. 4 illustrates the relation between the amount of BrdU incorporated and the intensity of green fluorescence.
Figure 4D:
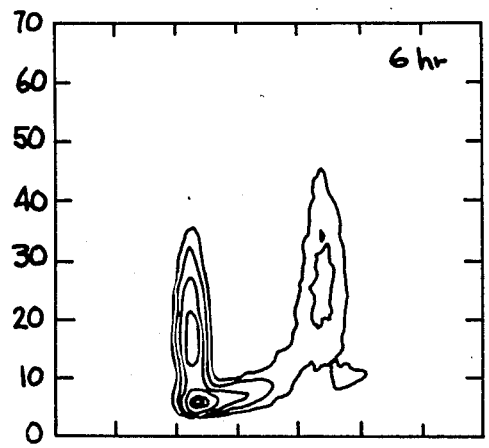
Figure 4E:
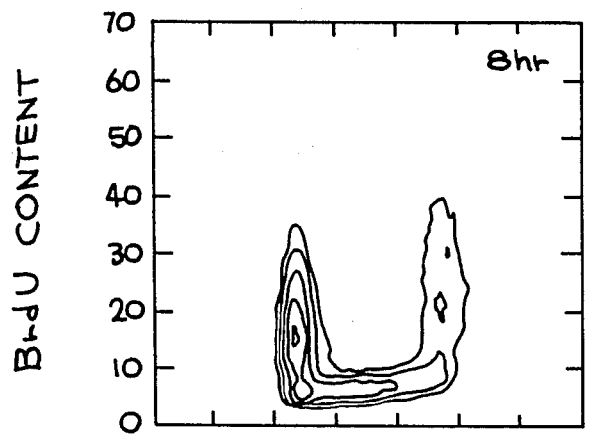
Figure 4F:
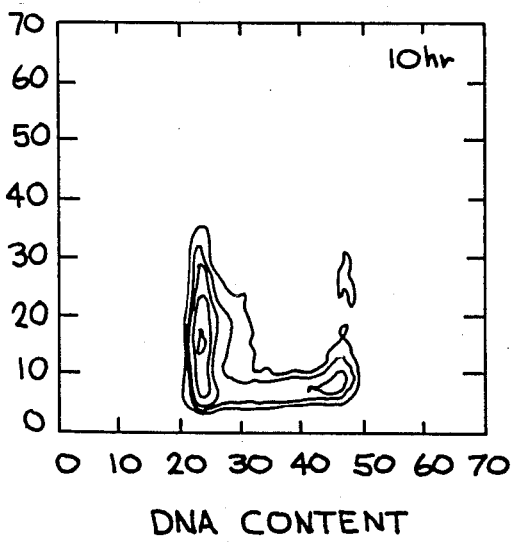
Figure 5A:
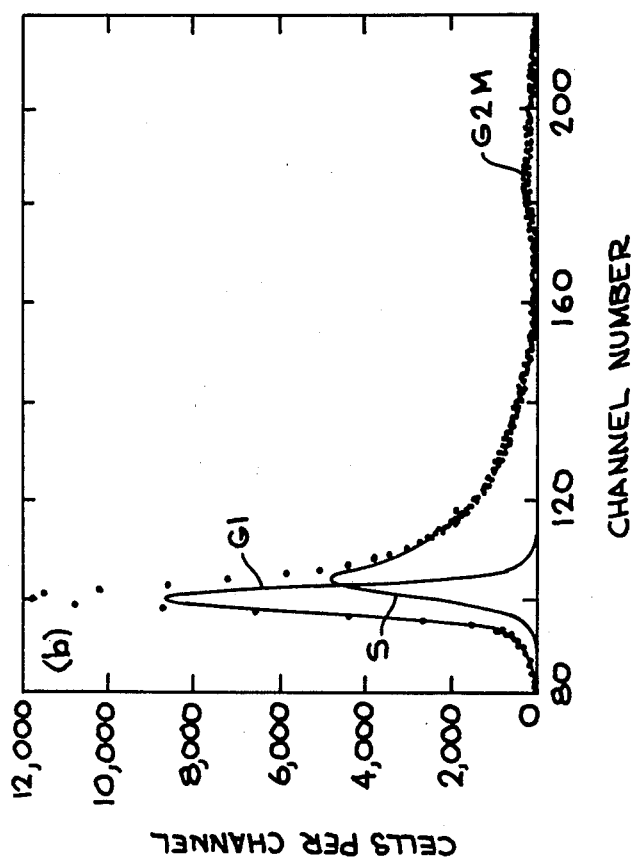
FIG. 5 shows cell cycle traverse rates for CHO cells.
Figure 5A:
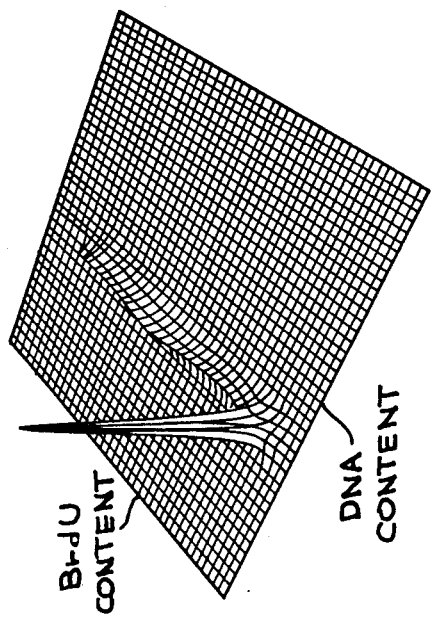
Figure 5B:
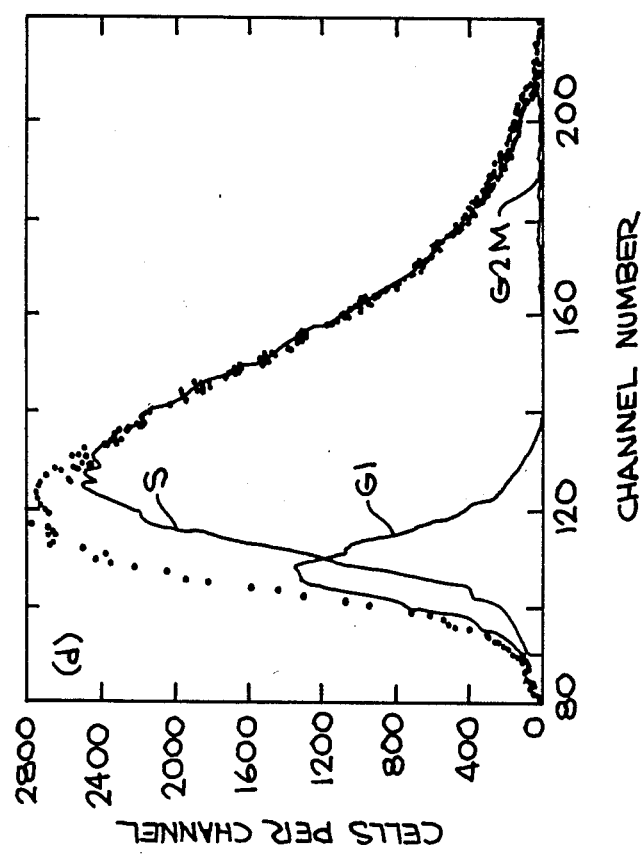
Figure 5B:
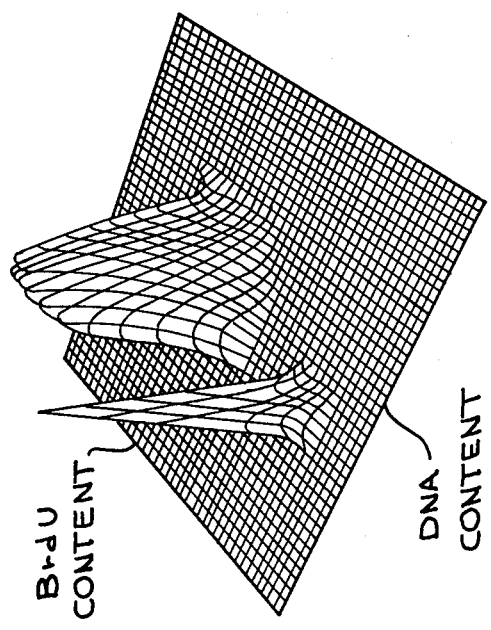
Figure 5C:
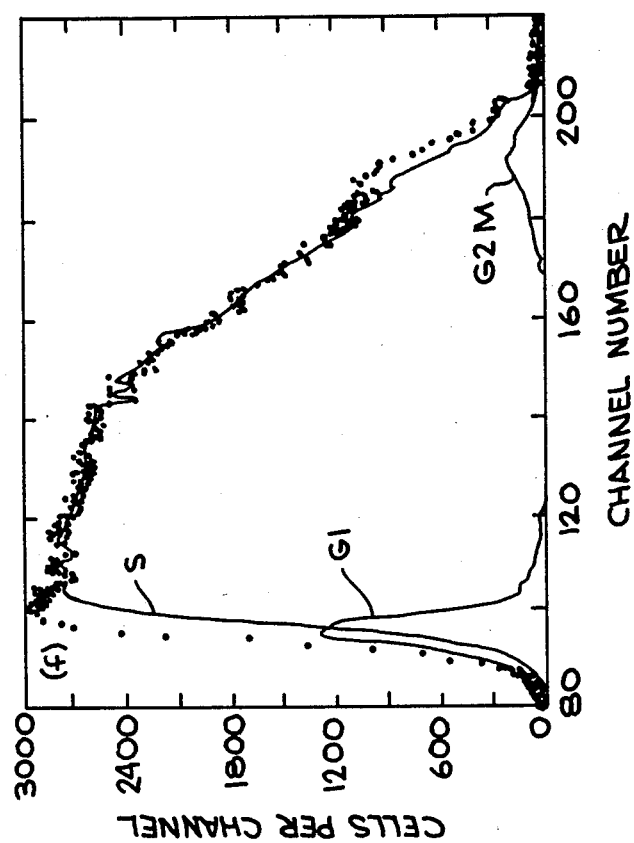
Figure 5C:
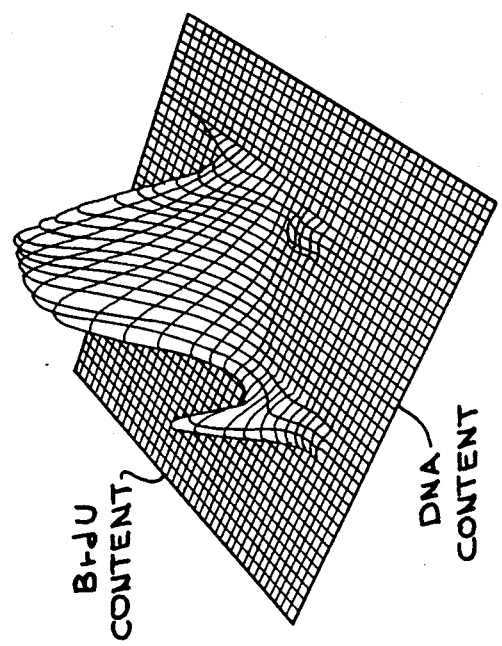
Figure 6A:
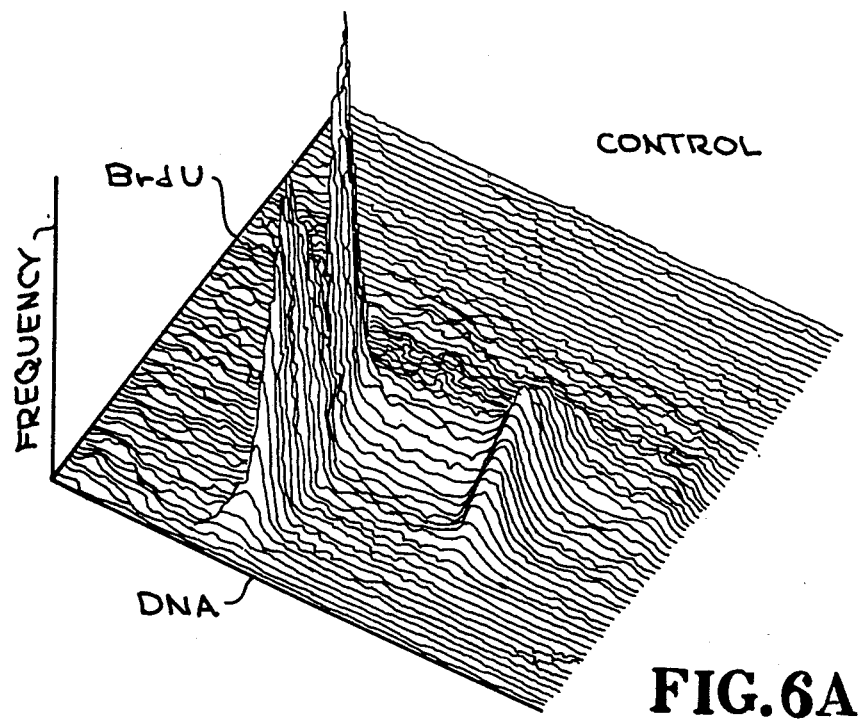
FIG. 6 depicts the bivariate DNA/BrdU distributions measured for mouse bone marrow cells.
Figure 6B:
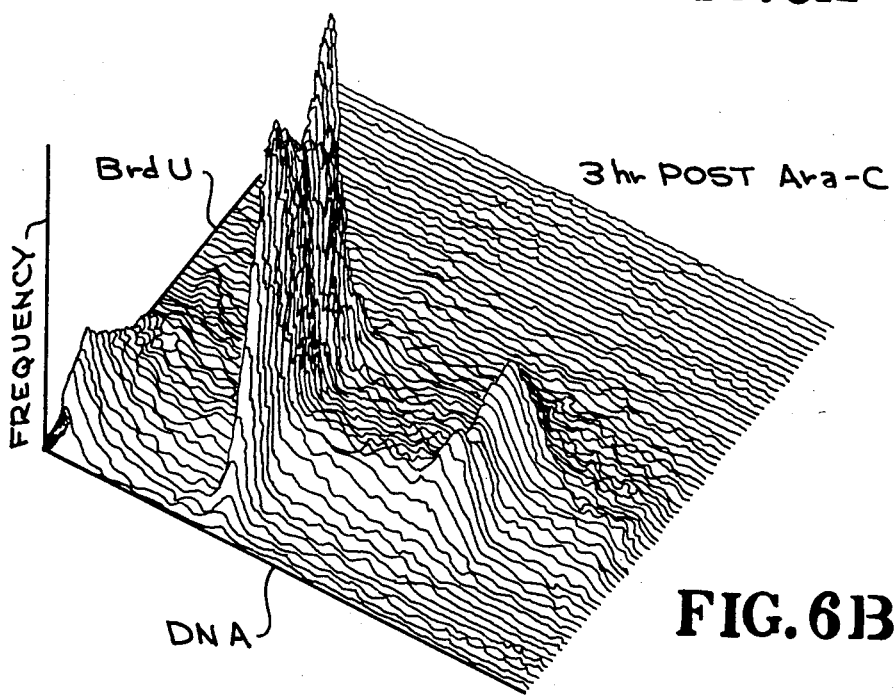
Figure 6C:
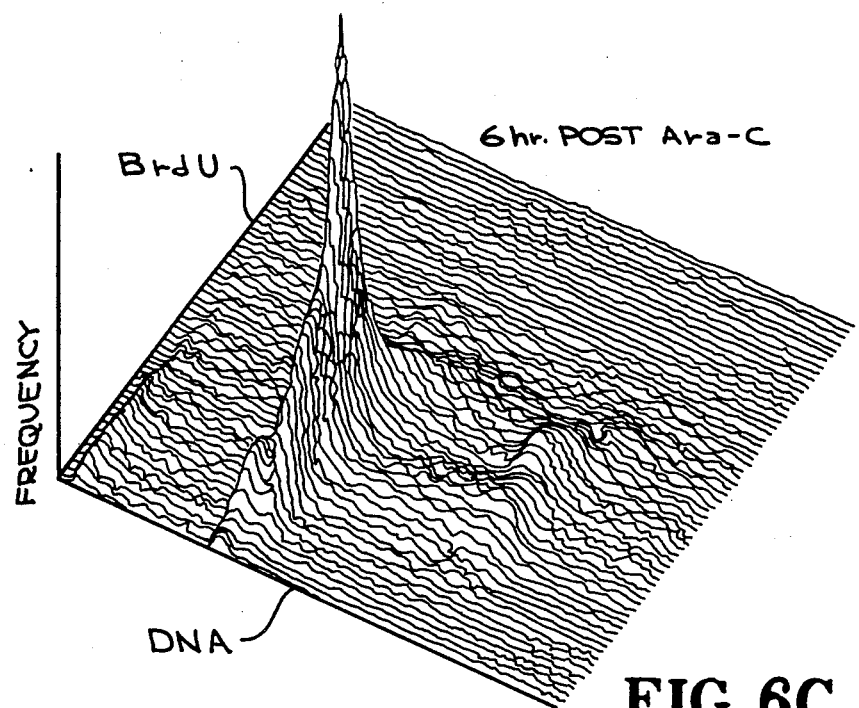
Figure 6D:
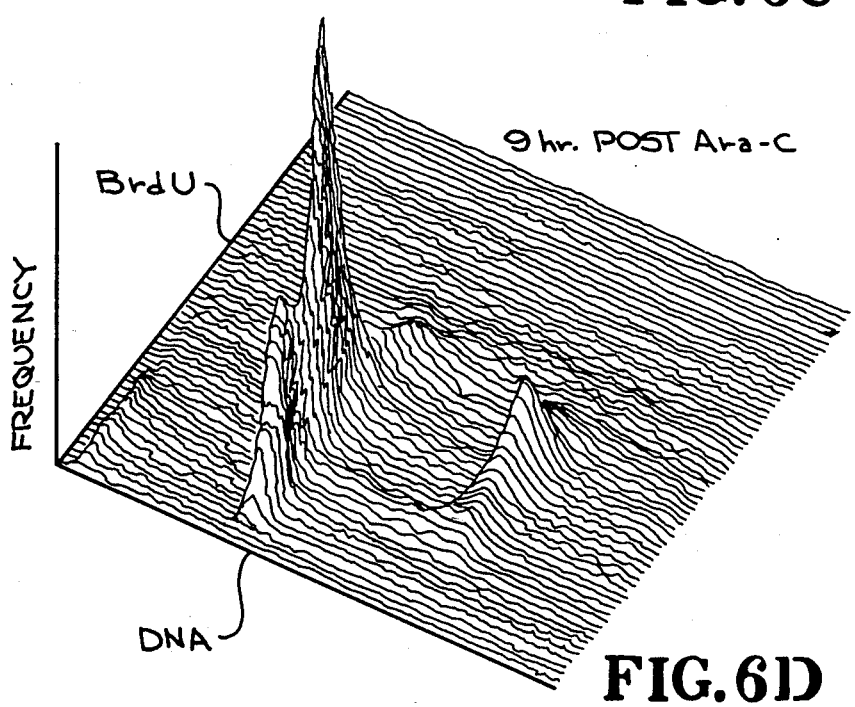

FIG. 3 illustrates the correlation between BrdU incorporated as measured by radioactivity of the tritiated BrdU as determined by liquid scintillation counting and green fluorescence as a measure of BrdU as measured by mab binding. A correlation of about 97% (r=0.97) confirms that a measure of the green fluorescence is an accurate measure of BrdU incorporation.

Cell cycle traverse rates can be calculated from the bivariate distribution curve of DNA/BrdU measured at specific time intervals following pulse labeling of the cells as illustrated in FIG. 4. The diagram (FIGS. 4A through 4F) shows bivariate DNA/BrdU distributions measured at two hour intervals for exponentially growing CHO cells after a 30 min exposure to 1 uM BrdU. The data indicate that the labeled CHO cells move out of the S phase into the $G_2M$ phase immediately or shortly after pulse labeling. About 8 hours after labeling, they are predominantly in the $G_2M$ and $G_1$ phases. By about 10 hours they start reentering S phase. As the cells go through mitosis, the green fluorescence is also seen to become divided between the divided cells. The BrdU content per cell is highest in mid-S phase and increases or decreases as the cohort of cells passes in or out of the $G_1$ phase. Cell cycle phase durations are quantitatively estimated from changes in the average values of BrdU per cell in mid-S phase and of BrdU per cell in the $G_1$ phase. These values may also be verified by measuring the amount of BrdU incorporated by measuring the radioactivity per cell.

FIGS. 5A through 5F show bivariate histograms of total DNA content (propidium iodide stain) vs. BrdU content (fluoresceinated antibody binding) for a control population of asynchronously growing CHO cells. The $G_1$ and $G_2M$ phases can be seen to be clearly separated from the S phase cells. The presence of $G_1$ and $G_2M$ peaks indicate a minor amount of nonspecific binding of the second antibody.

FIG. 6 shows isometric plots of the bivariate DNA/BrdU distributions measured for bone marrow cells obtained from control C3H mice and from araC-treated C3H mice labeled with BrdU 3, 6 and 9 hours after araC treatment. DNA content is plotted on the x axis, BrdU on the y axis and frequency on the z axis. All distributions show two two distinct peaks corresponding to $G_1$ DNA content—one at low green fluorescence and one at high green fluorescence. Cells sorted from the low green fluoresense peak were determined by microscopic analysis to be lymphocytes and blast cells, whereas cells sorted from the high green fluorescence peak were determined to be mostly well-differentiated granulocytes and macrophages. In the control population, cells sorted from mid-S phase were determined to be predominantly blast cells and thus to be associated with the low green fluorescence peak and with $G_1$-phase DNA content. The DNA/BrdU distribution measured for cells treated with BrdU 3 hours after araC treatment show that the majority of cells with an S-phase DNA content are characterized by low green fluorescence values, indicating negligible levels of DNA synthesis (i.e., BrdU incorporation). However, the DNA/BrdU distribution measured for cells treated with BrdU 6 hr after araC treatment shows that most of the cells with S-phase DNA content that did not incorporate BrdU have disappeared. The appearance in early S phase of a population incorporating substantial amounts of BrdU can also be seen in this distribution. The DNA/BrdU distributio measured for cells treated with BrdU 9 hr after araC treatment shows a substantial population of cells in early S phase that have incorporated a greater than normal amount of BrdU, suggesting an elevated rate of DNA synthesis.

The subject invention thus provides a sensitive method for the simultaneous measurement of the total cellular DNA content and of the level of DNA synthesis. The method is useful in many biological and biomedical investigations such as the detection of cells which have synthesized new DNA as part of their proliferation cycles; improved and accurate measurements of proliferation of cells in tumor and normal tissues, particularly monitoring the effects of drugs on proliferation in the course of human cancer therapy; the identification of cells that have repaired injury and the detection of unscheduled DNA synthesis. It provides for an improved detection of chemicals which are potentially damaging to DNA. It affords a mor sensitive method of detecting chromosome injury thereby facilitating the monitoring of human cells for evidence of genetic injury; and for the assay of BrdU in solution, particularly in competition ELISA pocedures to determine the level of BrdU in serum or other BrdU aqueous solutions as compared to the total cellular DNA content. Especially in cancer therapy involving drug treatment, the method permits the study of the fate of cells in all phases of the cell cycle during and following drug treatment. Labeling with BrdU after treatment permits assessment of the rate of Brd incorporation as well as the number of S-phase cells not incorporating BrdU, thereby enabling the determination of the cell-specific effects of a given drug. Pulse labeling of cells with BrdU before drug treatment permits the observation of the fate of both labeled (S-phase) and unlabeled ($G_1$ and $G_2M$) cells after treatment, and with extended pulse times (24 hours) the fraction of labeled and cycling cells can also be determined.

The foregoing description of the preferred embodiments of the subject invention have been presented for purposes of illustration and description and for a better understanding of the invention. It is not intended to be exhaustive or to limit the invention to the precise form disclosed; and obviously many modifications and variations are possible in light of the above teaching. The particular embodiments were chosen and described in some detail to best explain the principles of the invention and its practical applicatio to thereby enable others skilled in the relevant art to best utilize the invention in various embodiments and with various modifications as are suited to the particular use contemplated. It is intended that the invention be defined by the claims appended hereto.

We claim:

1. A method for the simultaneous measurement of total cellular DNA content and of incorporated labeled halodeoxyuridine comprising:
   providing halodeoxyuridine that is nonradioactively labeled;
   reacting cells with the nonradioactively labeled halodeoxyuridine;
   partially denaturing cellular DNA with a denaturing agent;
   adding to the reaction medium monoclonal antibodies reactive with the nonradioactively labeled halodeoxyuridine;
   reacting the bound monoclonal antibodies with a labeled second antibody;
   incubating the mixture with a DNA stain; and
   measuring simultaneously the intensity of the DNA stain and the amount of the bound labeled-antibody.

2. The method of claim 1 wherein said DNA stain is propidium iodide or Hoechst 33258.

3. The method of claim 1 wherein said halodeoxyuridine label is selected from the group consisting of an enzyme, fluorescent dye.

4. The method of claim 3 wherein said label is fluorescein or rhodamine.

5. The method of claim 1 wherein said second antibody is antimouse antibody.

6. The method of claim 5 wherein said antibody is labeled.

7. The method of claim 6 wherein said antibody label is an enzyme.

8. The method of claim of 7 wherein said enzyme is selected from the group consisting of alkaline phosphatase, beta-galactosidase and horse radish peroxidase.

9. The method of claim 6 wherein said antibody label is a fluorescent dye.

10. The method of claim 9 wherein said fluorescent dye is fluorescein or rhodamine.

11. The method of claim 1 wherein said halodeoxyuridine is bromodeoxyuridine, chlorodeoxyuridine or iododeoxyuridine.

12. The method of claim 11 wherein said halodeoxyuridine is bromodeoxyuridine.

13. A method for the bivariate analysis of cell cycle phase distribution of cellular DNA content comprising:
   pulse labeling cells with labeled halodeoxyuridine;
   denaturing the cellular DNA;
   reacting said cells with monoclonal antibodies IU-1 or IU-2;

incubating the cells with a second antibody conjugated to an enzyme label or a fluorescent label;
incubating the cells with propidium iodide or Hoechst 33258;
measuring simultaneously the bound halodeoxyuridine label and the bound propidium iodide or Hoechst 33258 cytometrically or spectrophotometrically as a measure of the incorporated HdU and of the total DNA in said cells; and
analyzing the bivariate distribution of total DNA and bound bromodeoxyuridine through the various phases of the cell cycle.

14. The method of claim 13 wherein said halodeoxyuridine is bromodeoxyuridine, chlorodeoxyuridine or iododeoxyuridine.

15. A method for the bivariate analysis of cell cycle traverse comprising:
pulse labeling cells with halodeoxyuridine;
reacting said cells with mabs IU-1 or IU-2;
incubating the cells with a second antibody conjugated to an enzyme label or a fluorescent label;
incubating the cells with a DNA stain;
measuring simultaneously at specified time intervals the bound halodeoxyuridine label and the bound DNA stain cytometrically or spectrophotometrically as a measure of the incorporated halodeoxyuridine and of the total DNA in said cells; and
analyzing the bivariate distribution of total DNA and bound bromodeoxyuridine through the various phases of the cell cycle.

16. The method of claim 15 wherein said halodeoxyuridine is bromodeoxyuridine, chlorodeoxyuridine, or iododeoxyuridine.

17. The method of claim 15 wherein said DNA stain is propidium iodide or Hoechst 33258.

18. A method for the measurement of halodeoxyuridine incorporation following drug treatment of an animal comprising:
treating said animal with a drug;
administering halodeoxyuridine to said drug-treated animal;
selectively removing cells from the body of said animal;
reacting said cells and monoclonal antibodies reactive with halodeoxyuridine;
incubating said cells with a second antibody conjugated to a label;
incubating said cells with a DNA stain;
measuring simultaneously at specified time invervals the bound halodeoxyuridine and the bound DNA stain cytometrically or spectrophotometrically as a measure of the incorporated halodeoxyuridine and of the total DNA in said cells; and
analyzing the bivariate distribution of total DNA and bound bromodeoxyuridine through the various phases of the cell cycle.

19. The method of claim 18 wherein said halodeoxyuridine is labeled.

20. The method of claim 19 wherein said label is a radionuclide.

21. The method of claim 20 wherein said halodeoxyuridine is bromodeoxyuridine or iododeoxyuridine.

22. The method of claim 18 wherein said second antibody label is a fluorescent dye or an enzyme.

23. The method of claim 22 wherein said dye is fluorescein or rhodamine.

* * * * *